United States Patent
Bohmer (10) Patent No.: US 7,785,898 B2
(45) Date of Patent: Aug. 31, 2010

(54) MATERNAL ANTIBODIES AS FETAL CELL MARKERS TO IDENTIFY AND ENRICH FETAL CELLS FROM MATERNAL BLOOD

(75) Inventor: Ralph M. Bohmer, West St Kilda (AU)

(73) Assignee: Genetic Technologies Limited, Fitzroy (AU)

( * ) Notice: Subject to any disclaimer, the term of this patent is extended or adjusted under 35 U.S.C. 154(b) by 1060 days.

(21) Appl. No.: 10/516,430

(22) PCT Filed: May 30, 2003

(86) PCT No.: PCT/AU03/00676

§ 371 (c)(1),
(2), (4) Date: Jun. 17, 2005

(87) PCT Pub. No.: WO03/102595

PCT Pub. Date: Dec. 11, 2003

(65) Prior Publication Data

US 2005/0287604 A1  Dec. 29, 2005

Related U.S. Application Data (60) Provisional application No. 60/385,170, filed on May 31, 2002.

(51) Int. Cl.
*G01N 33/564* (2006.01)
*G01N 33/53* (2006.01)

(52) U.S. Cl. .................. 436/506; 435/2; 435/7.2; 435/7.25; 435/287.2; 435/337; 435/372; 436/507; 436/513; 436/526; 436/538; 436/540; 436/541; 436/10; 436/63; 436/65; 436/172; 436/175; 436/177

(58) Field of Classification Search .......... 435/7.21, 435/7.23, 7.24, 7.92, 287.2, 2, 7.2, 7.25, 435/337, 372; 436/513, 517, 525, 528, 538, 436/540, 541, 546, 63, 65, 164, 172, 175, 436/177, 178, 506, 507, 526, 10
See application file for complete search history.

(56) References Cited

U.S. PATENT DOCUMENTS 3,817,837 A  6/1974  Rubenstein et al.

(Continued)

FOREIGN PATENT DOCUMENTS

WO    WO 91/14768    10/1991

(Continued)

OTHER PUBLICATIONS

Warwick et al., Detection strategy for maternal antibodies against paternal HPA-1 antigen, The Lancet 344: p. 64 (Jul. 2, 1994).*

(Continued)

*Primary Examiner*—Gailene R Gabel
(74) *Attorney, Agent, or Firm*—Sheridan Ross PC (57) ABSTRACT

The present invention provides methods for identifying and/or enriching fetal cells from maternal blood, using as fetal cell markers the antibodies that the mother produces against paternally inherited fetal antigens. The fetal cell-maternal antibody complexes are identified and isolated using labelled agents that bind to the maternal antibodies. The present invention also provides fetal cells, isolated by use of said maternal antibodies, as a source of fetal DNA for prenatal genetic diagnosis of the fetus.

15 Claims, 2 Drawing Sheets

U.S. PATENT DOCUMENTS

| | | | |
|---|---|---|---|
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,153,117 | A | 10/1992 | Simons |
| 5,447,842 | A * | 9/1995 | Simons .................. 435/6 |
| 5,503,981 | A | 4/1996 | Mueller et al. |
| 5,541,072 | A | 7/1996 | Wang et al. |
| 5,641,870 | A | 6/1997 | Rinderknecht et al. |
| 5,798,276 | A | 8/1998 | Haugland et al. |
| 5,830,912 | A | 11/1998 | Gee et al. |
| 5,969,157 | A | 10/1999 | Vicenzi |
| 6,130,101 | A | 10/2000 | Mao et al. |
| 6,162,931 | A | 12/2000 | Gee et al. |

FOREIGN PATENT DOCUMENTS

| | | |
|---|---|---|
| WO | 97/14028 | 4/1997 |
| WO | WO 02/26891 A1 | 4/2002 |

OTHER PUBLICATIONS

Bussel et al., Antenatal Treatment of Neonatal Alloimmune Thrombocytopenia, The New England Journal of Medicine 319: 1374-1378 (Nov. 24, 1988).*

Tsang et al., Optimum dissociating condition for immunoaffinity and preferential isolation of antibodies with high specific activity, Journal of Immunological Methods 138: 291-299 (1991).*

Sisson et al., An Improved Method for immobilizing IgG antibodies on protein A-agarose, Journal of Immunological Methods 127: 215-220 (1990).*

Holzgreve et al., Prenatal Diagnosis using Fetal Cells and Free Fetal DNA in Maternal Blood, Metabolic and Genetic Screening 28 (2): 353-362 (Jun. 2001).*

Wegmann et al., Allogeneic Placenta is a Paternal Strain Antigen Immunoabsorbent, The Journal of Immunology 122 (1): 270-274 (1979).*

Bianchi; "Fetal Cells in the Mother: From Genetic Diagnosis to Diseases Associated With Fetal Cell Microchimerism"; 2000; European Journal of Obstetrics & Gynecology and Reproductive Biology; 92; pp. 103-108.

Coppola et al.; "High-Performance Liquid Chromatography of Amino Acids, Peptides and Proteins: XCIII[a]. Comparison of Methods for the Purification of Mouse Monoclonal Immunoglobulin M Autoantibodies"; 1989; Journal of Chromatography; 476; pp. 269-290.

Nevens et al.; "Affinity Chromatographic Purification of Immunoglobulin M Antibodies Utilizing Immobilized Mannan Binding Protein"; 1992; Journal of Chromatography; 597; pp. 247-256.

Al-Mufti et al.; "Investigation of Maternal Blood Enriched for Fetal Cells: Role in Screening and Diagnosis of Fetal Trisomies"; 1999; American Journal of Medical Genetics; 85; pp. 66-75.

Douglas et al.; "Trophoblast in the Circulating Blood During Pregnancy"; Nov. 1959; American Journal of Obstetrics & Gynecology; V. 78; No. 5; pp. 960-973.

Folkersen et al.; "An Immunoprecipitation-Dissociation Technique for Large Scale Antibody Purification and an Antigen Consumption Electroimmunoassay for Antibody Quantitation. A Model Study with Antibodies to Pregnancy Zone Protein"; 1978; Journal of Immunological Methods; 23; pp. 127-135.

Hoffmann et al.; "Continuous Free-Flow Electrophoresis Separation of Cytosolic Proteins from the Human Colon Carcinoma Cell Line LIM 1215: A Non Two-Dimensional Gel Electrophoresis-Based Proteome Analysis Strategy"; 2001; Proteomics; 1; pp. 807-818.

Parker et al.; "Biophysical Characteristics of Anti-Gal$\alpha$1-3Gal IgM Binding to Cell Surfaces: Implications for Xenotransplantation"; Feb. 15, 2001; Transplantation; V. 71; pp. 440-446, No. 3.

Schröder; "Transplacental Passage of Blood Cells"; 1975; Journal of Medical Genetics; 12; pp. 230-242.

Sisson et al.; "An Improved Method for Immobilizing IgG Antibodies on Protein A-agarose"; 1990; Journal of Immunological Methods; 127; pp. 215-220.

Tsang et al.; "Optimum Dissociating Condition for Immunoaffinity and Preferential Isolation of Antibodies with High-Specific Activity"; 1991; Journal of Immunological Methods; 138; pp. 291-299.

Bohmer, R.M., "Fetal Cells from Maternal Blood: Purpose, Biological Questions, Technical Challenges," Intervirology 41:225-231 (1994).

Mowbray, et al., "Maternal Response to Paternal Trophoblast Antigens", American Journal of Reproductive Immunology, 1997, vol. 37, pp. 421-426.

Reed, et al., "The alloantibody response of pregnant women and its suppression by soluble HLA antigens and and anti-idiotypic antibodies", J. Reprod. Immunol., 1992, vol. 20, pp. 115-128.

Szekeres-Bartho, et al., Immunological relationship between the mother and the fetus, Intern. Rev. Immunol., Nov.-Dec. 2002, vol. 21, pp. 471-495.

International Search Report for International (PCT) Application No. PCT/AU03/00676, mailed Sep. 4, 2003.

* cited by examiner

Figure 1

*To isolate fetal cells that have not yet bound maternal antibodies or whose antigen-antibody complexes are masked*

Figure 2

*To isolate fetal cells that have already maternal antibodies bound to them, using an agent that labels those antibodies*

MATERNAL ANTIBODIES AS FETAL CELL MARKERS TO IDENTIFY AND ENRICH FETAL CELLS FROM MATERNAL BLOOD

This is a national stage filing under 35 U.S.C. §371(c) of PCT Application No. PCT/AU03/00676, filed May 30, 2003, which application claimed priority to U.S. Provisional Patent Application Ser. No. 60/385,170, filed May 31, 2002, the entire text of each of which is incorporated herein by reference.

FIELD OF THE INVENTION

The present invention relates to methods of identifying and enriching fetal cells from maternal blood.

BACKGROUND OF THE INVENTION

Fetal testing for chromosomal abnormalities is often performed on cells obtained using amniocentesis, or alternatively, Chorionic Villus Sampling (CVS). Amniocentesis is a procedure used to retrieve fetal cells from the fluid that surrounds the fetus. This relatively invasive procedure is performed after the 12th week of pregnancy. There is about 0.5% increased risk of miscarriage following amniocentesis. CVS is relatively less invasive, and can be performed as early as 10 weeks from conception. There is about 1% increased risk of miscarriage following CVS.

At least some fetal cell types such as platelets, trophoplasts, erythrocytes and leucocytes have been shown to cross the placenta and circulate in maternal blood (Douglas et al., *Am. J. Obstet. Gynec.* 78, 960-973, 1959; Schroder, *J. Med. Genet.* 12, 230-242, 1975). Maternal blood represents a non-invasive source of fetal cell types, however the isolation of fetal cells from maternal blood is hampered by the scarcity of such fetal cells in the maternal circulation, as well as the lack of a marker that identifies all fetal cells, rather than merely a sub-population. A pan-fetal cell-specific antibody is not available.

SUMMARY OF THE INVENTION

One aspect of the present invention provides methods for identifying and/or enriching fetal cells from maternal blood, wherein fetal cell-maternal antibody complexes are identified or recovered. These methods utilize a reagent that detects or isolates different types of fetal cells, in particular a maternally-produced antibody that is specific for a paternally-inherited fetal antigen.

In the course of a normal pregnancy, the mother mounts a humoral immune response against paternally inherited fetal antigens. A complex network of anti-HLA antibodies, anti-idiotype (anti-anti-HLA) antibodies and soluble HLA antigens exists in maternal plasma. The maternal antibodies can bind specifically to fetal cells expressing paternally inherited HLA antigens. The antibodies are unique to a particular pregnancy except that they may be useful to identify fetal cells in subsequent pregnancies in which the fetus has some of the same paternally inherited antigens.

Fetal cells are identified and retrieved from maternal blood using maternal antibodies, which are produced by the mother against paternally inherited fetal antigens present on the surface of a fetal cell. The paternally inherited antigens are unique fetal cell markers, which are targeted for the isolation of fetal cells from maternal blood.

The method of identifying and/or isolating a fetal cell from maternal peripheral blood is carried out by detecting maternal antibodies that are specifically bound to the fetal cells among the nucleated cells isolated from maternal blood.

Antibodies are bound to fetal cells already at the time of blood collection, due to the exposure of fetal cells to maternal plasma from the time the cells crossed over into the maternal circulation. Additionally or alternatively, a preparation of peripheral blood mononuclear cells is contacted with maternal plasma, an antibody-containing fraction of said plasma, or a purified reactive antibody preparation isolated from said plasma, under conditions permitting formation of an antibody complex with the fetal cells.

The maternal antibody-bound fetal cell complex is identified with a secondary antibody or other molecule that binds to human antibodies. The physical isolation of fetal cells is achieved by a cell isolation procedure based on cellular labels. Examples include fluorescence-activated cell sorting, using a fluorescence label on the secondary antibody. In another example, the secondary label can be coupled to paramagnetic beads and the fetal cells isolated with a magnet.

Maternal antibodies may also be bound to a subpopulation of maternal cells in the circulation. Therefore, additional prior or subsequent steps are optionally carried out to either physically remove such maternal cells, or to distinguish them from fetal cells during analysis.

The enrichment method of the present inventive results in at least a 10-fold, more preferably at least a 100-fold, more preferably at least a 1,000-fold, more preferably at least a 10,000 and even more preferably at least a 100,000-fold increase in the numbers of fetal cells relative to maternal cells. Absolute purification (100% fetal cells) may be possible using the inventive method, however such stringency is not required for the present purpose. The present invention is not to be limited to an absolute purification of fetal cells.

If needed, the successful isolation of fetal cells can be confirmed using an independent marker for fetal cells. In the case that the fetus is male, this can be a Y-chromosome-specific marker. In case the fetus is female, fetal cell isolation can be confirmed using polymorphic markers such as SNPs or the HLA system.

Fetal cells isolated or enriched using the methods of the present invention can be used for prenatal diagnosis of fetal genetic disorders. Basically, all diagnostic procedures can be performed that are commonly being performed using fetal cells obtained by invasive procedures such as amniocentesis of CVS. Examples include of such genetic disorders include, but are not limited to, Down's syndrome, trisomy 18, trisomy 13, sickle cell anaemia, 21-hydroxylase deficiency, cystic fibrosis, and the like.

Although it is particularly preferred that the methods of the present invention are performed to enrich or identify human fetal cells, the methods could also be used for enriching or identifying fetal cells from any placental mammal such as, but not limited to, horses, cattle, dogs, etc.

A second aspect of the present invention provides a composition comprising fetal cells when isolated or obtained by the inventive method described herein.

DETAILED DESCRIPTION OF THE INVENTION

General Techniques and Definitions

Figure 1:
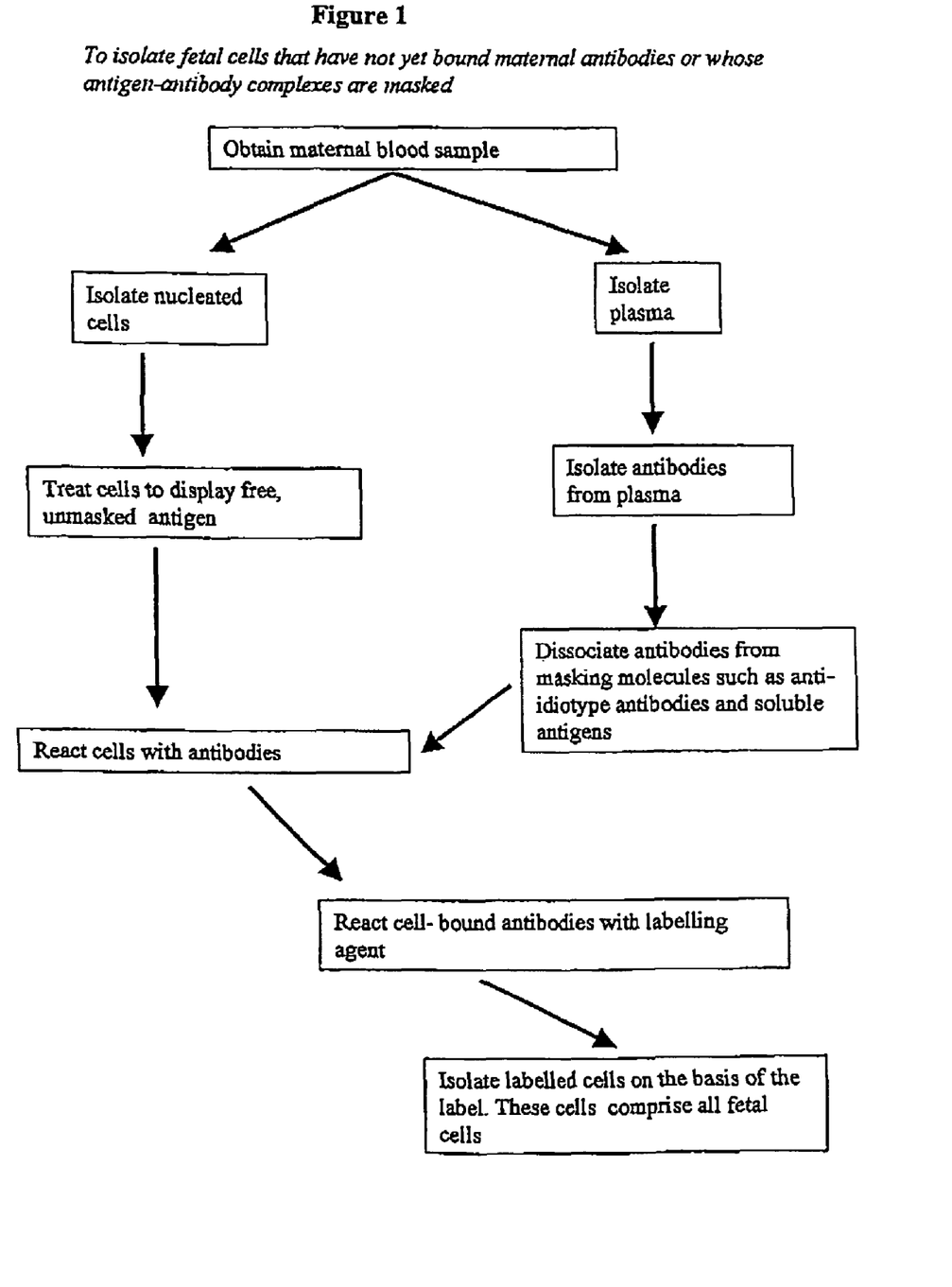
FIG. 1: Scheme for isolating fetal cells that have not yet bound maternal antibodies or whose antigen-antibody complexes are masked.
Figure 2:
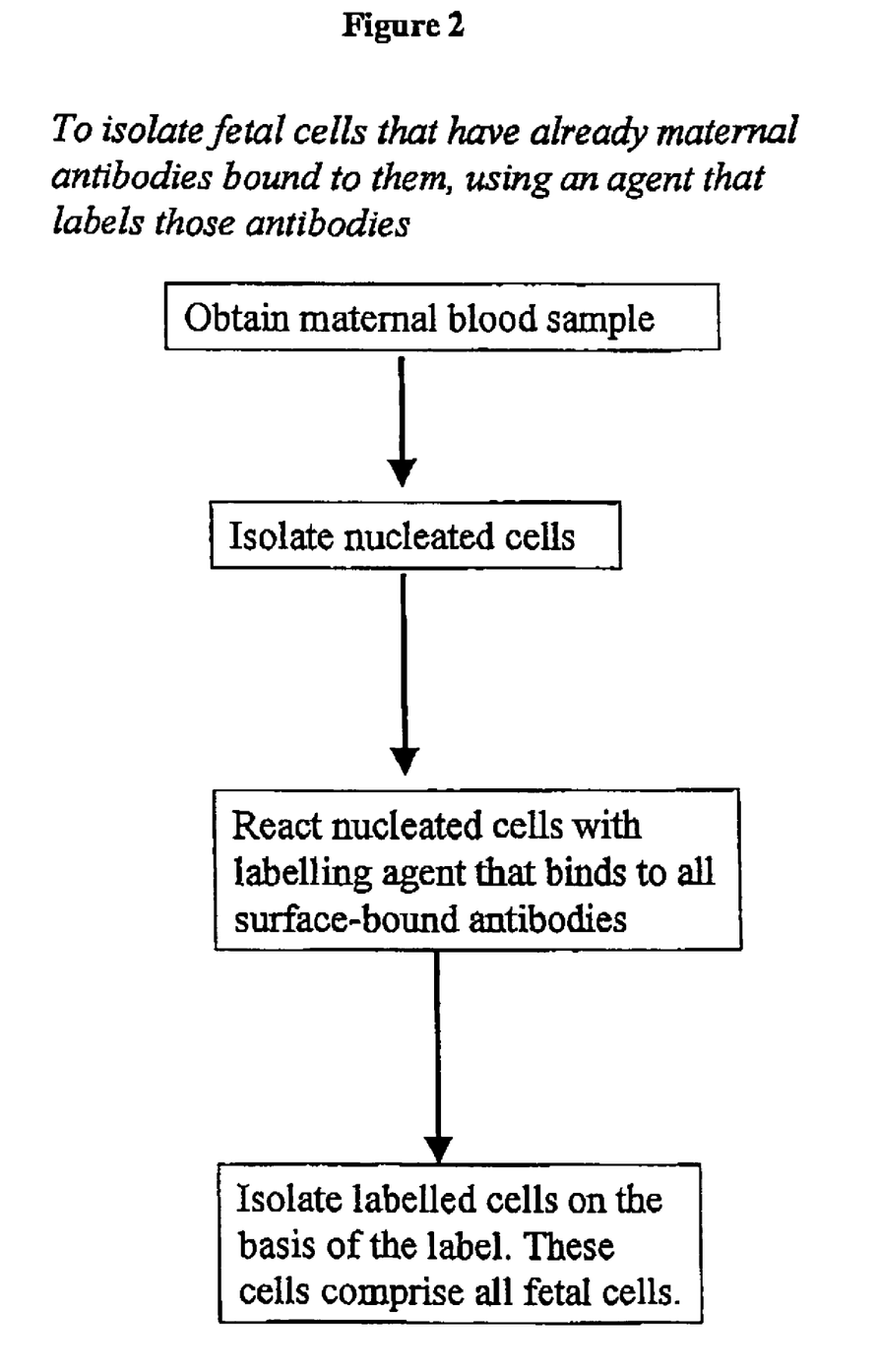
FIG. 2: Scheme for isolating fetal cells that have maternal antibodies bound to them, using an agent that labels those antibodies.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples or preferred embodiments described herein. Functionally equivalent products, compositions and methods are clearly within the scope of the invention, as described herein.

Unless the context requires otherwise or specifically stated to the contrary, integers, steps, or elements of the invention recited herein as singular integers, steps or elements clearly encompass both singular and plural forms of the recited integers, steps or elements.

Unless specifically stated otherwise, each feature described herein with reference to a particular aspect or embodiment of the invention shall be taken to apply mutatis mutandis to each and every other aspect or embodiment of the invention.

Unless specifically defined otherwise, all technical and scientific terms used herein shall be taken to have the same meaning as commonly understood by one of ordinary skill in the art (e.g., in cell culture, molecular genetics, immunology, nucleic acid chemistry, hybridisation techniques and biochemistry).

Unless otherwise indicated, the recombinant DNA and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

All publications referred to herein are incorporated herein in their entirety.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

As used herein the term "derived from" shall be taken to indicate that a specified integer is obtained from a particular source albeit not necessarily directly from that source.

As used herein, the term "enriching" or "enrichment" indicates that the ratio of the number of fetal cells to the number of maternal cells in a sample subjected to the inventive method described herein has been increased relative to this ratio in a maternal blood sample from which the cells were derived.

Preferred Embodiments

1. Direct Isolation of Maternal Antibody-fetal Complexes from Maternal Plasma

One embodiment of the present invention provides methods for identifying and/or enriching fetal cells present in maternal blood, wherein fetal cell-maternal antibody complexes that are present in the maternal blood are identified or recovered.

The identification and/or recovery and/or isolation of a fetal cell from maternal peripheral blood is preferably carried out by a process that comprises detecting, isolating or recovering maternal antibodies that are specifically bound to the fetal cells among the nucleated cells isolated from maternal blood. The maternal antibodies are bound to fetal cells before blood collection, or at the time of blood collection, due to the exposure of fetal cells to maternal plasma during pregnancy, eg, from the time fetal cells cross over into the maternal circulation, thereby forming a maternal antibody-bound fetal cell complex. For example, a complex comprising anti-(HLA antigen)-Ig bound to a fetal cell, or alternatively, anti-anti-(HLA antigen)-Ig bound to a fetal cell, is isolated from a cell sample derived from a maternal blood sample.

In an alternative embodiment of the present invention there is provided a method of enriching fetal cells from maternal blood, the method comprising contacting a fetal cell-maternal antibody complex in maternal blood with an agent capable of binding to a human antibody in said complex and isolating the agent.

In a preferred embodiment, the maternal blood is obtained previously from a pregnant female subject. Preferably, the subject method further comprises the first step of providing a sample of maternal blood.

2. Isolation of Fetal Cells from Cellular Fractions of Maternal Blood Using Antibody-containing Fraction of Maternal Blood The identification and/or recovery and/or isolation of a fetal cell from maternal peripheral blood is also carried out by a process that comprises contacting cells derived from maternal blood with an antibody-containing fraction of maternal plasma for a time and under conditions sufficient to permit formation of a maternal antibody-bound fetal cell complex. For example, a complex comprising anti-(HLA antigen)-Ig bound to a fetal cell is formed.

In another embodiment, there is provided a method of enriching fetal cells from a maternal blood sample, the method comprising contacting a cell preparation from maternal blood comprising fetal cells with an antibody-containing fraction of maternal plasma, or a preparation of purified reactive antibody from maternal plasma, for a time and under conditions sufficient to permit formation of a maternal antibody-bound fetal cell complex, contacting the complex with an isolatable agent capable of binding to a human antibody in said complex and isolating the agent.

In another embodiment, there is provided a method of enriching fetal cells from a sample of cells obtained from maternal blood, the method comprising contacting cells in the sample with maternal antibodies for a time and under conditions sufficient to permit formation of a maternal antibody-bound fetal cell complex, and recovering the complex, wherein the maternal antibodies comprise a maternally-produced antibody specific for a paternally-inherited fetal antigen, contacting the maternal antibody-bound fetal cell complex with an isolatable agent capable of binding to a maternal antibody in said complex and isolating the agent, to thereby recover the complex.

In a particularly preferred embodiment, the present invention provides a method of enriching fetal cells from a maternal blood sample, the method comprising contacting a preparation of PBMCs with maternal plasma, an antibody-containing fraction of said plasma, or a purified or partially purified antibody preparation isolated from said plasma, under conditions permitting formation of a maternal antibody-bound fetal cell complex and recovering the complex, wherein the maternal antibodies comprise a maternally-produced antibody specific for a paternally-inherited fetal antigen. Preferably, the maternal antibody-bound fetal cell complex is contacted with an agent capable of binding to a maternal antibody in said complex and isolating the agent, to thereby recover the complex.

In an even more particularly preferred embodiment, the present invention provides a method of enriching fetal cells from a maternal blood sample, the method comprising the steps of;
i) isolating peripheral blood mononuclear cells from the sample;
ii) contacting the cells from i) with an antibody from a maternal plasma sample under conditions sufficient to permit maternally produced antibodies specific for paternally-inherited fetal antigens to bind fetal cells;
iii) contacting the complexed cells from ii) with an agent capable of forming a complex with maternal antibodies; and
iv) recovering cells bound to agent-maternal antibody complexes.

For the purposes of clarification, the terms "cell" or "cellular fraction" or "PBMCs" or "PBMC fraction" or similar term used herein refers to nucleated cells isolated from maternal blood, such as, for example, following purification of blood on Ficoll. As will be known to the skilled artisan, a preparation of PBMCs or isolated PBMCs is a fraction of the maternal blood that comprises a mixture of cells, including fetal cells. Accordingly, the fetal cells are isolated with maternal PBMCs in such a nucleated cellular fraction.

The term "antibody-containing fraction of maternal blood" shall be taken to include any purified or partially purified fraction of maternal blood that comprises an antibody-producing cell, antibody, or immunoglobulin, such as, for example, IgM or IgG. Accordingly, an antibody-containing fraction of maternal blood clearly includes an IgM or IgG fraction isolated from maternal plasma.

In a preferred embodiment of the inventive method, the maternal plasma and/or antibody-containing fraction of maternal plasma are/is obtained from a blood sample of a pregnant female subject and reacted with a cell preparation derived from the same blood sample.

In a preferred embodiment, the maternal plasma or other antibody-containing fraction of maternal plasma and/or the cellular fraction of maternal plasma are/is obtained previously from a pregnant female subject.

Preferably, the subject method further comprises the first step(s) of providing a sample of maternal blood, maternal plasma or other antibody-containing fraction of maternal blood. Alternatively, or in addition, a cellular fraction of maternal blood (e.g., PBMCs) is obtained previously from the subject.

Even more preferably, the subject method further comprises the first steps of providing a sample of maternal blood and isolating a PBMC fraction and/or plasma or an antibody fraction therefrom according to any standard procedure known to those skilled in the art. This embodiment of the present invention also clearly encompasses the provision of maternal blood and isolation of plasma therefrom.

Maternal Blood Sample

As used herein, the term "maternal blood sample" shall be taken to mean any sample of blood that includes maternal antibodies and fetal cells.

Preferably, the maternal blood sample consists of a sample of peripheral blood taken directly from a pregnant female.

More preferably, the sample is obtained from a pregnant woman in her first trimester of pregnancy.

The sample can be a blood sample that is prevented from clotting such as a sample containing heparin or, preferably, ACD solution.

The sample is preferably used fresh, or stored at 0° C. to about 4° C. until use to minimize degradation of its components.

The number of fetal cells in the sample varies depending on factors including the age of the fetus. Typically, from 10 to 30 ml of maternal blood provides sufficient fetal cells upon separation from maternal cells. The skilled artisan will be aware of quantities of other samples that are equivalent to 10-30 ml maternal blood in terms of maternal antibody and/or fetal cell content.

Preparation of Maternal Antibodies

1. General Techniques

Maternal antibodies are isolated or partially-purified from maternal blood, or purified free of other proteins, using any technique known in the art. This procedure is performed at any stage of the inventive method. Preferably nucleated cells and maternal antibodies are prepared independently from maternal plasma, and recombined to produce an immune complex for isolating fetal cells.

The maternal antibody preparation process ensures that the plasma antibodies are sufficiently concentrated, and capable of binding fetal cell surface antigens and/or any agent that is required to identify and/or isolate the fetal cells.

Examples of antibody purification procedures include, but are not limited to, hydroxylapatite chromatography, gel electrophoresis, dialysis, and affinity chromatography. Affinity chromatography is the preferred purification technique.

2. Isolation of Ig Fractions

Protein A and/or protein G affinity chromatography is preferably used to isolate IgG. The matrix to which an affinity ligand is attached is most often agarose or Sepharose, (Pharmacia, Sweden) but other matrices are available. Mechanically stable matrices, such as, for example, controlled pore glass or poly(styrenedivinyl)benzene, allow for faster flow rates and shorter processing times than can be achieved with agarose. Other techniques for antibody purification such as fractionation on an ion-exchange column, ethanol precipitation, Reverse Phase HPLC, chromatography on silica, chromatography on heparin-Sepharose™, chromatography on an anion or cation exchange resin (such as a polyaspartic acid column), chromatofocussing, SDS-PAGE, and ammonium sulfate precipitation are also useful in this context.

As will be known to the skilled artisan, protein-A and protein-G bind to the Fc potion of IgG. Accordingly, immunoglobulin G (IgG) is amenable to purification by affinity chromatography on Protein-A Sepharose or Protein-G Sepharose. The initial step of binding is performed under native conditions so as not to perturb any protein-protein interaction (e.g., Protein-A or Protein-G bound to antibody, or alternatively, an antibody-antibody interaction). Antibodies are eluted from the Protein-A or Protein-G using a dissociating buffer, such as, for example, a buffer comprising a high salt concentration (e.g., 3M $MgCl_2$ in HEPES pH 7.2) that releases the antibodies as unbound components.

In an alternative embodiment, the antibody fraction is separated from other constituents by affinity chromatography on Kaptive-M™-Sepharose. Those skilled in the art are aware that IgM binds to Kaptiv-M, the active constituent of which is a peptidomimetic.

Alternatively, MBP-Sepharose can be used. Those skilled in the art are aware that MBP may bind to mannose residues present on the IgM Fc5µ region, and, as a consequence, is specific for IgM. The initial step of binding is performed under native conditions so as not to perturb any protein-protein interaction (e.g., MBP bound to antibody, or alternatively, an antibody-antibody interaction). IgM is eluted from the affinity matrix using a dissociating buffer, such as, for example, a buffer comprising a high salt concentration (e.g., 3M $MgCl_2$ in HEPES pH 7.2) that releases the antibodies as unbound components.

In an alternative embodiment, the antibody fraction is isolated using caproylic acid and ammonium sulphate precipitation. As will be known to the skilled artisan, these agents provide preparations that comprise essentially Ig. By dissolving the Ig fraction in a dissociating buffer such as, for example, a high-salt buffer (e.g., 3M $MgCl_2$ in/HEPES pH 7.2), the antibodies are released as unbound components. The antibody fractions are then separated by SEC, for example, using the dissociating buffer as an eluant to maintain the IgG and IgM components as unbound components.

In an alternative embodiment, immunoglobulin is subjected to free-flow electrophoresis under denaturing conditions. Plasma isolated from maternal blood is clarified and the bulk of plasma proteins are precipitated under conditions that leave Ig and some α2-macroglobulins in solution. The Ig fraction is then precipitated and redissolved in a suitable buffer, applied to a free-flow electrophoresis (FFE) device (e.g., Octopus, Tecan) for separation by continuous solution-phase isoelectric focusing as described essentially by Hoffman et al., *Proteomics* 1, 807-818, 2001). Fractions are obtained, preferably corresponding to a range of about 0.01 to about 0.05 pH units per fraction, and exchanged into a suitable buffer (e.g., PBS) using PD-10 or fast-desalting columns (Amersham Biosciences) to test for viability.

Alternatively, antibody fractions are transferred into a high-salt buffer for coupling to CNBr—Sepharose or NHS-Sepharose (Pharmacia) for further use.

3. Further Purification of Immunoglobulins

Antigen reactive antibodies (i.e., antibodies that bind to maternal antibodies against paternal antigens present on the surface of a fetal cell) are preferably prepared by dissociation from a complex with a soluble HLA antigen and/or an anti-idiotypic antibody.

Accordingly, in a preferred embodiment, the antibody preparation is partially purified or purified free or substantially free of antigens. This is generally achieved by dissociating antibody-antigen complexes present in the maternal blood. As will be apparent to the skilled artisan, such a procedure is not to be performed on a maternal blood sample when a complex comprising fetal cells and maternal antibodies is to isolated directly or recovered from maternal blood, however such a procedure may be similar to that subsequently used to dissociate such a complex once isolated or recovered from the maternal blood. Extraction of the antibody fraction in a dissociating buffer, such as, for example, a buffer comprising a high salt concentration, will release most bound antigens.

In a particularly preferred embodiment, high molecular weight antibodies (e.g, IgG having a molecular mass of about 150 kDa, or IgM having a molecular mass of about 950 kDa) are separated from salt and low molecular mass peptide HLA antigens of about 9-40 residues in length, by desalting in a low-salt buffer. Soluble HLA antigens are dissociated from anti HLA antibodies, thereby releasing reactive antibodies, by first incubating plasma from maternal blood with caprylic acid, to thereby precipitate the bulk of plasma proteins without affecting Ig and some $\alpha_2$-macroglobulins. Following this initial precipitation, the Ig fraction is precipitated, such as, for example, using ammonium sulfate (Tsang et al., *J. Immunol. Methods* 138, 291-299, 1991), redissolved in a suitable buffer (e.g., HEPES pH 7.2) comprising high salt (e.g., 3M magnesium chloride) and 25% (v/v) ethylene glycol in buffer. This solution is then rapidly desalted to remove the salt and peptide HLA antigens, for example, by chromatography using PD-10 columns or FAST-desalting columns (Amersham Biosciences) in Tris-buffered saline as the mobile phase. A buffer such as PBS cannot be used with magnesium chloride, as phosphate-based buffers precipitate in the presence of magnesium-based salts. The high-molecular weight fraction obtained is substantially free of peptide HLA antigens and is desalted for further use. The purified anti-HLA antibodies are then reacted with the maternal blood cell preparation containing some target fetal cells, for a time and under conditions sufficient for a complex to occur, and the complexes are isolated as described herein.

The antibody can be purified further to obtain preparations that are more homogeneous or substantially homogeneous, for use in the method described herein. For example, hydrophobic interaction chromatography (HIC), particularly low pH HIC (LPHIC) as described in the U.S. Pat. No. 5,641,870, is used for further purification of antibodies. In particular, LPHIC is useful for removing a correctly folded and disulfide bonded antibody from unwanted contaminants (e.g., incorrectly associated light and heavy fragments).

4. Enrichment of Specific Antibodies that Bind to Paternal Antigens on Fetal Cells Preferably, the maternally produced antibodies specific for paternally-inherited fetal antigens are enriched before use in the methods of the invention. In one embodiment, isolated maternal antibodies are exposed to a large panel of HLA antigens bound to, for example, a solid support. Antibodies that bind known HLA antigens are separated from those that do not bind HLA antigens. Since it is highly unlikely that there are only a few, if any, maternal antibodies that bind maternal HLA antigens. As a consequence, most of the HLA antibodies that are bound are specific for HLA antigens inherited from the father.

If the HLA type of the mother is known, or determined using standard techniques, use of a large panel of HLA antigens in the purification step preferably excludes maternal HLA antigens, thereby ensuring that the remaining HLA binding antibodies are directed to HLA antigens inherited from the father. In addition, if the HLA type of the father is known, or determined using standard techniques, a panel of HLA antigens can be selected such that it comprises paternally-derived antigens, preferably excluding any HLA antigens that are maternally-derived or in a common with a maternally-derived antigen.

In a particular embodiment of the antibody isolation by HLA antigens, multiplex color-coded beads (Luminex, Life-Codes) are used, wherein each color type is conjugated with a particular HLA antigen. The color-coded multiplex beads are used to identify and isolate maternal antibodies to paternally inherited HLA antigens from maternal blood samples. For example, if the maternal HLA type is known, multiplex beads excluding those maternally-derived antigens are used to isolate or purify and determine the paternally inherited fetal HLA antigens, and/or to isolate captured fetal specific antibodies by flow sorting of the corresponding multiplex beads.

Alternatively, once the fetal HLA type is known, magnetic capture beads conjugated with one or several of the fetal HLA antigens is used to isolate the fetus-specific antibodies from maternal plasma.

A further aspect of the present invention extends to any isolated maternal antibody or purified Ig fraction thereof that binds to a paternal antigen or paternally-inherited fetal antigen when isolated or obtained by the inventive method described herein.

A still further aspect of the present invention provides for the use of an isolated maternal antibody or Ig fraction thereof that binds to a paternal antigen or paternally-inherited fetal antigen in medicine, such as, for example, in the isolation, identification or enrichment of fetal cells or as a marker for a fetal cell in maternal blood, or in the preparation of a reagent for any one or more of said uses in medicine.

Agents that Form Complexes with Maternal Antibodies Bound to Fetal Cells

The maternal antibody-bound fetal cell complex is identified using a readily detectable and/or readily isolatable agent, such as, for example, a secondary antibody, antibody fragment, or other molecule that binds to human antibodies (eg. goat anti-human Ig, or a polypeptide that binds to IgM or IgG, such as, for example, a polypeptide selected from the group consisting of: protein A, protein G and protein L.).

The term "agent" means a molecule that is capable of forming a complex with a maternal antibody when bound to a fetal cell, including a ligand of the maternal antibody or a reporter molecule that binds to the maternal antibody. By "reporter molecule" is meant an agent that provides a detectable signal.

Preferably, the agent does not bind molecules in maternal blood other than a maternal antibody.

In one embodiment the agent is an antibody, or fragment or derivate thereof, which is directed against the maternal antibody.

The antibody may be a polyclonal or monoclonal antibody.

Preferably, the antibody is a monoclonal antibody. Monoclonal antibodies can be raised in one species against the binding sites of antibodies of another species. Those skilled in the art are aware that any antibody raised in one species against an immunoglobulin from another species will provide an antibody that binds generally to the immunoglobulin from that other species. Preferably, the fetal cells are human cells, and the agent binds to any human antibody. Such antibodies against human antibodies are well known in the art. Examples include, but are not limited to, goat anti-human IgG, mouse anti-human IgG, goat anti-human IgM, mouse anti-human IgM, goat anti-human IgA, and mouse anti-human IgA.

Those skilled in the art are aware of several techniques for routinely producing monoclonal antibodies. Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982).

Polyclonal antibodies are also useful in the methods of the invention. Monospecific polyclonal antibodies are preferred. Suitable polyclonal antibodies can be prepared using methods well known in the art.

The antigen-binding portion or a monoclonal antibody or polyclonal antibody may be a part of an antibody (for example a Fab fragment) or a synthetic antibody fragment (for example a single chain Fv fragment [ScFv]). Accordingly, such fragments are clearly useful as agents within the present context.

Fragments of antibodies, such as Fab and F(ab)$_2$ fragments may also be used as can genetically engineered antibodies and antibody fragments.

Antigen specificity is conferred by variable domains and is independent of the constant domains. Accordingly, recombinant antibody fragments comprising one or more variable domains, such as, for example, Fab-like molecules; Fv molecules; single-chain Fv (ScFv) molecules where the $V_H$ and $V_L$ partner domains are linked via a flexible oligopeptide, and single domain antibodies (dAbs) comprising isolated V domains, are also useful as agents in the present context.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

Fab, Fv, ScFv and dAb antibody fragments can all be expressed in and secreted from *E. coli*, thereby permitting the production of large amounts of the said fragments.

In a particularly preferred embodiment, the agent is an anti-idiotypic antibody that binds to a maternal antibody that is specific for a paternal antigen. Such anti-idiotypic antibodies are generally isolated from the maternal blood as immune complexes comprising the maternal antibody and the anti-idiotypic antibody, optionally further comprising the paternal antigen e.g., as a soluble HLA antigen.

Antibody-anti-idiotypic antibody complexes are isolated from the Ig fraction of maternal blood as described herein above for antibody preparation in general, and dissociated to obtain reactive antibodies. For example, the antibody complexes can be isolated by chromatography using an Ig-specific ligand (e.g., Protein-G, Protein-A, Protein-L, Kaptive-M™-Sepharose, or MBP-Sepharose) under native conditions so as not to perturb any protein-protein interaction, and then dissociating the antibody complexes using a dissociating buffer, such as, for example, a buffer comprising a high salt concentration (e.g., 3M MgCl$_2$ in HEPES pH 7.2) that releases the antibodies as unbound components. As with the preparation of antibodies in general, caprylic acid and ammonium sulphate precipitation can also be used to isolate anti-idiotypic antibodies complexed with antibodies against paternal antigens, and then the anti-idiotypic antibodies are released by dissociating the antibody complexes in a dissociating buffer such as, for example, a high-salt buffer (e.g., 3M MgCl$_2$ in/HEPES pH 7.2), the antibodies are released as unbound components. The antibody fractions are then separated by SEC, for example, using the dissociating buffer as an eluant to maintain the IgG and IgM components as unbound components. If the anti idiotypic antibody is of the IgM or IgG class, those anti-idiotypic antibodies are bound to a solid support (CNBr- or NHS-Sepharose or other amine reactive bead) to maintain their separation from the bulk maternal IgM or IgG factions, wherein the separate antibody fraction will no longer have idiotypic antibody bound.

Extraction of the antibody fraction in a dissociating buffer, such as, for example, a buffer comprising a high salt concentration, will also release most bound antigens. High molecular weight antibodies (e.g, IgG having a molecular mass of about 150 kDa, or IgM having a molecular mass of about 950 kDa) are separated from salt and low molecular mass peptide HLA antigens of about 9-40 residues in length, by desalting in a low-salt buffer.

Preferably, the anti-idiotypic antibody recognizes a maternal antibody against a paternal HLA antigen.

In another embodiment, the agent is a non-antibody polypeptide that binds to an antibody. Such polypeptides are known in the art and include, but are not limited to, protein A, protein G and protein L.

The term "protein G" as used herein shall be taken to include a protein comprising one or more natural IgG-binding domains of protein G, a hybrid or fusion protein comprising an IgG-binding domain of a native or naturally-occurring protein G, or a mutant or variant of a native or naturally-occurring protein G that retains the ability of native protein G to bind IgG, or a fragment of a native or naturally-occurring protein G that retains the ability of native protein G to bind IgG.

The term "protein A" as used herein shall be taken to include a protein comprising one or more natural IgG-binding domains of protein A, a hybrid or fusion protein comprising an IgG-binding domain of a native or naturally-occurring protein A, or a mutant or variant of a native or naturally-occurring protein A that retains the ability of native protein A to bind IgG, or a fragment of a native or naturally-occurring protein A that retains the ability of native protein A to bind IgG.

The term "protein L" as used herein shall be taken to include a protein comprising one or more natural antibody light-chain-binding domains of protein L, a hybrid or fusion protein comprising an antibody light-chain-binding domain of a native or naturally-occurring protein L, or a mutant or variant of a native or naturally-occurring protein L that retains the ability of native protein L to bind an antibody light-chain, or a fragment of a native or naturally-occurring protein L that retains the ability of native protein L to bind an antibody light-chain.

Isolatable or Detectable Labels

The agent that binds to the maternal antibody is bound or conjugated to an isolatable or detectable label capable of providing a detectable signal (e.g., a fluorescent label, a color tag, a radioactive label, a paramagnetic particle, a chemoluminescent label, biotin, streptavidin, or a label that is detected through a secondary, enzymatic or binding step).

As used herein, the term "isolatable label" or "detectable label" shall be taken to mean a molecule that enables an agent-maternal antibody-fetal cell complex to be detected, such as, for example, by providing a detectable signal or physical property to facilitate partitioning, sedimentation or other separation of a complex bound to the label from other compositions of matter in a sample.

A wide variety of labels and conjugation techniques are known and reported extensively in both the scientific and patent literature. Preferred detectable labels include, but are not limited to, a fluorescent label, a radioactive label, a paramagnetic particle, a chemoluminescent label. The present invention clearly contemplates the use of a label that is detected by virtue of the binding of a secondary ligand, or alternatively, by virtue of an enzymatic reaction that is dependent on the label. The skilled artisan will be aware of other suitable labels for binding to the agents of the invention, or will be able to ascertain such, using routine experimentation. Patents disclosing such labels include U.S. Pat. Nos. 3,817, 837; 3,850,752; 3,939,350; 3,996,345; 4,277,437; 4,275,149; and 4,366,241. The binding of such labels to the agent is performed using standard techniques known to those skilled in the art.

Preferred labels are fluorescent moieties such as, for example, those described in Molecular Probes Handbook of Fluorescent Probes And Research Chemicals (R. P. Haugland 8th Ed., CD-ROM, 2001). Particularly preferred fluorescent moieties are xanthenes (e.g., fluoresceins, rhodamines and rhodols), Sulfonated xanthenes, such as, for example, those disclosed in U.S. Pat. No. 6,130,101 and UK 9611997.9 are particularly preferred. Fluorinated xanthenes, such as, for example, those disclosed in U.S. Pat. No. 6,162,931 are also preferred. Coumarins, such as, for example, sulfonated coumarins (e.g., U.S. Pat. No. 5,969,157) or fluorinated coumarins (e.g., U.S. Pat. No. 5,830,912), or alternatively, cyanines (e.g., WO 02/26891) can also be used.

The agent may be labeled indirectly using a variety of methods known in the art, For example, a "secondary antibody" (a directly labelled antibody that binds specifically to the agent) can be used to detect an agent consisting of an antibody. Alternatively, the agent can be derivatized using biotin, in which case labeled streptavidin can be used to bind the label to the derivatized agent.

The present invention clearly extends to the use of a coded multiplex bead conjugated to a HLA antigen to identify a maternal antibody that binds to a paternally-inherited fetal HLA antigen. Such multiplex beads coupled with HLA antigens are commericially available (LifeMatch, Orchid). Such coded multiplex beads conjugated with HLA antigens are particularly useful for isolating specific maternal antibodies directed against paternally-inherited fetal HLA antigens that correspond to the paternal HLA antigen. The multiplex beads are coded and identified with a fluorescent label. Antibody bound to the bead is detectable with a label that binds specifically to the antibody (e.g., a secondary fluorescent label that attaches to the antibody). The specific beads having bound that antibodies of interest can be flow sorted to recover the bound antibodies.

Recovery and/or Detection of Maternal Antibodies Bound to Fetal Cells

Fetal cells bound to maternal antibodies are recovered directly from a maternal blood sample, or alternatively, following ex vivo binding of a maternal antibody preparation with maternal blood or a cellular fraction thereof (e.g., PBMC fraction). The fetal cells bound by maternal antibody and labelled agent are partitioned or isolated by a process that selects for the label.

Preferred means for detecting the reporter molecule include, for example, fluorescence-activated cell sorting (FACS) using a fluorescence label on the secondary antibody, or applying a magnet field or paramagnetic field to a magnetic bead or paramagnetic bead that is attached to secondary antibody.

As described herein, an "agent" that is preferably detectably labelled is employed in these recovery and/or detection procedures. Useful techniques include, not are not limited to, cell sorting, especially fluorescence-activated cell sorting (FACS), by using an agent bound to a substrate (e.g., a plastic surface, as in panning), or by using an agent bound to a solid phase particle/bead which is isolated on the basis of the properties of the particles/beads (e.g., colored latex beads or magnetic particles/paramagnetic particles).

For the recovery or detection of fetal cells by cell sorting, the agent is labelled directly or indirectly with a substance, such as, for example, a colored or fluorescent dye that is detected using a cell sorter. Preferably, the dye is a fluorescent dye. A large number of different dyes/moieties/labels are known in the art, including fluorescein, rhodamine, Texas Red, phycoerythrin, and the like. Any detectable substance which has the appropriate characteristics for the cell sorter may be used (e.g., in the case of a fluorescent dye, a dye which can be excited by the sorter's light source, and an emission spectra which can be detected by the cell sorter's detector).

For the recovery or detection of fetal cells using solid-phase particles, any particle with the desired properties may be utilized. For example, large particles (e.g., greater than about 90-100 □m in diameter) may be used to facilitate sedimentation. Preferably, the particles are "paramagnetic particles" (i.e., particles that can be collected by applying a magnetic field to the sample, thereby facilitating partitioning of the particles and bound complexes from the liquid phase). Magnetic particles are now commonly available from a variety of manufacturers including Dynal Biotech (Oslo, Norway). An example of magnetic cell sorting (MACS) is provided by Al-Mufti et al. (1999).

For the recovery or detection of fetal cells using an agent bound to a substrate, the agent is preferably adsorbed or bound directly (e.g., by covalent linkage, ionic interaction or van der Waals interaction) to the substrate. Preferably, the substrate is the surface of a plastic plate or flask, and the agent is adsorbed directly to the surface. Adsorption is easily accomplished for most agents, and when the agent is an antibody, adsorption is accomplished by simply contacting a solution containing the antibody with the substrate. Alternatively, a modified substrate may be used, such as, for example, a substrate modified by conjugation with avidin or streptavidin, or an agent modified by conjugation with biotin, or an amine-derivatized substrate activated with a bifunctional crosslinking agent. Preferably, the agent is adsorbed to the substrate by contacting a solution containing the agent on the substrate.

Preferably, fetal cell isolation is confirmed by a process that comprises using an independent marker to detect a fetal cell. For example, if the fetus is male, a marker consisting of a Y-chromosome-specific marker is used according to art-recognized procedures to confirm that the isolated cell population comprises fetal cells. On the other hand, if the fetus is female, a marker consisting of a polymorphic marker such as, for example, a SNP, or a marker that is specific for the HLA system is used according to art-recognized procedures to confirm that the isolated cell population comprises fetal cells.

Depletion of Maternal Cells

Recovery or detection of fetal cells may be enhanced or aided by the depletion of maternal cells or a maternal cell type present in the maternal blood sample. This depletion is performed prior to, during, or following, the steps of contacting the maternal antibody-bound fetal cells with the agent and recovering the agent-antibody-fetal cell complex. Those skilled in the art are aware that maternal cell types in maternal blood include erythrocytes, B cells, T cells, monocytes, macrophages and dendritic cells. In this respect, maternal antibodies may also be complexed with, or bound to, a subpopulation of maternal cells in circulation, thereby reducing their availability for complexing with the fetal cells in maternal blood ex vivo. The present invention clearly encompasses additional steps performed prior to, during, or following, the isolation of maternal plasma or an antibody or antibody-containing fraction of maternal plasma, wherein such steps physically separate maternal cell and fetal cell populations, deplete the maternal cell population, deplete the maternal cells of at least one maternal cell type, or distinguish maternal cells from fetal cells during analysis.

Preferably, the maternal cell population or maternal cells are depleted by exposing a maternal blood sample or a nucleated cellular fraction thereof to an antibody that binds to a cellular marker on the maternal cell for a time and under conditions sufficient to form an antibody-maternal cell complex and isolating the antibody-maternal cell complex. As with other embodiments described herein, the antibody-maternal cell complex is preferably isolated by contacting said complex with a readily detectable and/or a readily isolatable agent. Preferably, such an agent is different from the agent used to isolate, enhance or enrich a fetal cell population, such as, for example, to permit maternal cell depletion and fetal cell enrichment to be performed simultaneously.

For example, mononuclear cells (e.g., a PBMC preparation comprising fetal cells) can be isolated from the blood of pregnant women by density gradient centrifugation. To further enrich the proportion of fetal cells present in the sample, blood cell types that are not likely to originate from the fetus (e.g., mature leukocytes) are removed. In one embodiment, such cells are selectively removed by incubating the cells with specific antibodies that bind a maternal antigen. Antibodies that bind markers of maternal nucleated blood cells are well known in the art. Preferably, the antibodies bind an antigen present on the cell surface of a maternal blood mononuclear cell, however do not bind to a maternal or paternal antigen on a fetal cell.

Preferably, the antibody is attached to a solid support. Solid supports include magnetic beads, plastic flasks, plastic dishes, columns and the like.

By employing an affinity purification step to selectively remove such maternal cells, the total number of maternal nucleated cells remaining in the cell suspension is reduced, and the proportion of fetal cells present in the sample is enhanced.

Unmasking of Maternal Antibodies

In some cases, maternal antibodies that attach to fetal cells during their exposure to maternal plasma in vivo may be masked, or otherwise rendered unavailable for binding to the agent and subsequent isolation or detection using the label bound thereto. This masking may arise, for example, by an unknown mechanism that protects fetal cells from maternal immune attack. For example, plasma antibodies may be masked or inactivated by complexing with secondary, anti-idiotype antibodies, or with soluble HLA antigen.

It is also possible that maternal antibodies bound to a fetal cell may fix complement and destroy some of the fetal cells to which they bind while in the maternal circulation. In such cases, only those fetal cells that are bound by large numbers of maternal antibodies would be available for isolation.

Accordingly, in a preferred embodiment of the present invention, cells in maternal blood (including maternal and fetal cell populations) are unmask bound antibodies, thereby enhancing the subsequent recovery or detection of fetal cells via the maternal antibodies bound thereto.

In one embodiment, cells from maternal blood, and antibodies from maternal plasma, are extracted as distinct fractions from the maternal blood sample, treated as appropriate to unmask the maternal antibodies, and then recombined for further enhancement of fetal cells in accordance with the inventive method. Such "pre-treatments" are discussed in further detail below.

The present invention clearly encompasses a preferred step of exposing cells isolated from maternal blood to a maternal derived antibody preparation (see below) under conditions that do not allow complement lysis, e.g., in the presence of a chelating agent such as EDTA, to thereby enhance the number of fetal cells in the maternal blood sample or a fraction thereof.

Dissociation of Fetal Cells from Maternal Antibodies

Preferably, the inventive method according to any embodiment described herein, particularly any preceding embodiment, further comprises isolating the fetal cells from the maternal antibody, preferably by disrupting the maternal antibody-bound fetal cell complex to release the fetal cells. Preferably the released fetal cells are viable fetal cells. In a particularly preferred embodiment, the fetal cells are cultured in vitro for a time and under conditions sufficient to permit their use in diagnosis of a genetic disorder or a predisposition for a genetic disorder, or for karyotyping of the fetal cells.

In one embodiment, a cell sample from maternal blood comprising maternal antibody-fetal cell complexes is treated so as to remove bound antibody from the cells, subjected to a brief culture phase during which cells are allowed to fully express and display HLA antigens, and optionally, to proliferate. Following culture, fetal cells are identified, such as, for example, by contacting the cellular fraction with a maternal plasma-derived antibody preparation. In addition, cultured cells may be subjected to pre-purification steps such as those described herein, to deplete maternal cells such as B cells from the cellular fraction. Alternatively, or in addition, the antibodies may be unmasked as described herein above.

In accordance with this embodiment, antibodies are detached from the surface of a cell whilst maintaining cell viability, using a number of procedures known to those skilled in the art. By "maintaining cell viability" is meant that sufficient viable cells are recoverable for further growth, by passaging of the cells using standard tissue culture techniques.

Preferably, such techniques are performed within 4-72 hours from the time at which the maternal blood sample is taken from a female subject, since cells grown in culture may readily shed cell-surface bound antibodies after this time.

In one embodiment, non covalently bound proteins are rapidly detached by digestion with trypsin (i.e. "trypsinization") or other suitable protease, or alternatively, by mixed-protease digestion of cell-surface proteins. Alternatively, or in addition, reduction of cell-surface disulfide bridges may be carried out.

Trypsin is known to cleave proteins adjacent to basic amino acid residues, namely lysine and arginine. In accordance with this embodiment, trypsinization is carried out for a time and under conditions sufficient to cleave all or most cell surface proteins that are not sterically hindered by other molecules, thereby progressively digesting away peptides from the cell surface to facilitate the presentation of new HLA complexes after tissue culture. For trypsinization of cell-surface proteins, fetal cells obtained from maternal blood preparations and grown by established tissue culture techniques are washed in a suitable media or buffer solution that is compatible with the cells, such as, for example, phosphate-buffered saline (PBS) and then incubated in media comprising trypsin (e.g., 0.1% (w/v) trypsin/0.02% (w/v) Versene solution in PBS) and incubated for a time and under conditions sufficient for proteolysis to occur. Exemplary incubation conditions comprise an incubation at about 37° C. for between about 1 minute to about 20 minutes, more preferably for about 1-5 minutes. The incubation time is dependant on the extent of cleavage required to abolish bound antibody without adversely affecting cell viability, which is determined empirically in trial assays. Once digestion is complete, the cells are subjected to a separation techniques, such as, for example, a centrifugation step that results in collection of the cells as a cell pellet. Cells are then cultured, such as, for example, by plating on a suitable solid medium for continuous culture using established techniques.

Mixed protease digestion is preferred, as it is more efficient than mere trypsinization. This is because the enzyme specificity achieved is very broad, as a consequence of using a number of different enzymes. By virtue of the mix of proteases used, aromatic amino acids (i.e., phenylalanine, tyrosine and tryptophan), hydrophobic amino acids and many non-specific sites can be cleaved, not merely adjacent to lysine and arginine residues. For mixed proteolysis, fetal cells are subjected to similar conditions as for trypsinization, however the trypsin is substituted for a mixture of proteases, such as, for example, a mixture comprising a protease selected from the group consisting of trypsin, papain, pronase, elastase, collagenase and chymotrypsin. Other combinations of proteases are not excluded.

Those skilled in the art are aware that reduction of cell-surface disulfide bridges cleaves the disulfide bond between two cystine residues in a protein, thereby converting the cystine to two free-SH cysteine residues in the peptide chain. In this manner, most proteins unfold, destroying their tertiary structure. Non-covalently linked proteins bound to membrane proteins are thereby removed from the cell surface. The presentation of new HLA complexes occurs after further tissue culture of the cells. For reduction of cell-surface disulfide bridges, cells are incubated in the presence of a suitable reducing agent, such as, for example, dithiothreitol (DTT) or Tris(2-carboxyethyl)phosphine (TCEP). TCEP is a stronger reducing agent than DTT and may be advantageous by reducing cell-surface bound proteins more rapidly when compared to DTT. Reduction is generally performed using a concentration of reducing agent from about 0.1 mM to about 50 mM, and for an incubation period of about 1 minute to about 30 minutes. To determine the suitability of any reducing agent and to establish suitable incubation conditions, isolated cells from maternal blood are cultured under established conditions and washed in a suitable medium or buffer solution (e.g., PBS), incubated in media comprising a range of concentrations of reducing agent and incubated for various periods of time. After incubation, cells are then washed to remove reducing agent, then placed in a culture medium, and incubated for a time and under conditions sufficient for cell growth or division to occur. The conditions under which cell growth or division is maintained are selected. Upon further growth, isolated fetal cells are monitored for the presence of fetal hemoglobin, or the transferrin receptor CD71, using monoclonal antibodies that bind specifically to those proteins (Bianchi et al., *Eur. J. Obstet Gynecol. Reprod. Biol.* 92, 103-108, 2000). A similar procedure has been used with success for dissociating anti-Gal α1-3Gal antibodies from cell surfaces (Parker et al., *Transplantation* 71, 440-446, 2001).

Uses of Isolated Fetal Cells

The isolated fetal cells prepared as described herein are suitable for use in any and all prenatal diagnostic tests that can be performed using a fetal cell obtained via known invasive procedures, such as, for example, amniocentesis or chorionic villus sampling. The present invention clearly provides for the use of an isolated or cultured fetal cell produced according to any embodiment described herein in medicine, such as, for example, to determine a genetic disorder or predisposition to a genetic disorder in a fetus. Diagnostic procedures known to the skilled artisan can be performed on fetal cells isolated by the inventive method for determining any one or more of a number of routinely screened genetic disorders, such as, for example, Down's syndrome, trisomy 18, trisomy 13, sickle cell anaemia, 21-hydroxylase deficiency, cystic fibrosis, and the like.

Accordingly, a further aspect of the present invention provides a method of detecting a genetic disorder in an animal subject, said method comprising performing a process that comprises determining or identifying a fetal cell and/or enriching fetal cells from maternal blood or a nucleated cellular fraction thereof according to any embodiment described herein. As will be apparent to the skilled artisan, wherein the fetal cell carries and/or expresses a gene that is indicative of a genetic disorder or predisposition to a genetic disorder, the presence and/or expression of said gene is also indicative of that genetic disorder or predisposition in the intact fetus from which the fetal cell is derived.

Although it is particularly preferred that the method of the present invention is used to enrich or identify human fetal cells, or to screen for genetic deficiencies in a human fetus, the invention is equally useful for enriching or identifying fetal cells from any placental mammal such as, but not limited to, horses, cattle, dogs etc. The invention is also useful for the genetic screening of any placental mammal based upon such isolated or enriched fetal cells.

In one embodiment of the present invention, the isolated fetal cells or a fraction enriched in fetal cells, are used directly for prenatal genetic testing. Alternatively, they are cultured to expand cells numbers and to facilitate karyotype analysis.

Because fetal cells obtained by the methods of the invention comprise the same genetic DNA make up of the somatic cells of the fetus, these fetal cells can be analysed for abnormalities using techniques known in the art, wherein an abnormality that is detected is diagnostic of that abnormality in the intact fetus.

Analysis of fetal cells for a genetic disorder or a predisposition for a genetic disorder can be performed on any cellular material derived from a fetal cell that permits a defect to be detected. Preferably, this material is nuclear DNA, however, at least is some instances it may be informative to analyse RNA or protein from the isolated fetal cells. Furthermore, the DNA may comprise a genomic gene or RNA that is not translated, or the an informative non-transcribed marker (e.g., a repetitive DNA marker or SNP).

In one preferred embodiment, chromosomal abnormalities are detected. By "chromosomal abnormality" is meant any gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome which can be detected by DNA analysis.

Other genetic disorders which can be detected by DNA analysis are known such as 21-hydroxylase deficiency or holocarboxylase synthetase deficiency, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranching enzyme deficiency (Type III glycogen storage disease). These and other genetic diseases are mentioned in The Metabolic and Molecular Basis of Inherited Disease, 7th Edition, Volumes I, II and III, Scriver, C. R., Beaudet, A. L., Sly, W. S., and Valle, D. (eds), McGraw Hill, 1995. Clearly, any genetic disease where the gene has been cloned and mutations detected can be analysed.

Genetic assay methods include the standard techniques of karyotyping, analysis of methylation patterns, restriction fragment length polymorphism assays and PCR-based assays, fluorescence in situ hybridisation (FISH) as well as other methods described below.

Chromosomal abnormalities can be detected by karyotyping which is well known in the art. Karyotyping analysis is generally performed on cells, which have been arrested during mitosis by the addition of a mitotic spindle inhibitor such as colchicine. Preferably, a Giemsa-stained chromosome spread is prepared, allowing analysis of chromosome number as well as detection of chromosomal translocations.

The genetic assays may involve any suitable method for identifying mutations or polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, namely capable of detecting a mutation at another position or gene that is known to be linked to one or more of the mutant positions. The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the polymerase chain reaction (PCR) method and modifications thereof.

Amplification of DNA may be achieved by the established PCR methods or by developments thereof or alternatives such as the ligase chain reaction, QB replicase and nucleic acid sequence-based amplification.

An "appropriate restriction enzyme" is one that will recognise and cut the wild-type sequence and not the mutated sequence or vice versa. The sequence which is recognised and cut by the restriction enzyme (or not, as the case may be) can be present as a consequence of the mutation or it can be introduced into the normal or mutant allele using mismatched oligonucleotides in the PCR reaction. It is convenient if the enzyme cuts DNA only infrequently, in other words if it recognises a sequence that occurs only rarely.

In another embodiment, a pair of PCR primers is used which hybridizes to either a wild-type gene or a mutant/variant gene associated with a particular disorder or predisposition, but not to both alleles. The presence or absence of amplified DNA is indicative of the wild-type or mutant genotype (and hence phenotype).

A preferred embodiment employs similar PCR primers but, as well as hybridising to only one of the wild-type or mutant sequences, they introduce a restriction site that is not otherwise there in either the wild-type or mutant sequences.

To facilitate subsequent cloning of amplified sequences, primers may have restriction enzyme sites appended to their 5' ends. Thus, all nucleotides of the primers are derived from the gene sequence of interest or sequences adjacent to that gene except the few nucleotides necessary to form a restriction enzyme site. Such enzymes and sites are well known in the art. The primers themselves can be synthesized using techniques that are well known in the art. Generally, the oligonucleotide primers are synthesized machines using art-recognized procedures and equipment that is commercially available.

PCR techniques that utilize fluorescent dyes may also be used to detect genetic defects in DNA from fetal cells isolated by the methods of the invention. These include, but are not limited to, the following five techniques.

i) Fluorescent dyes can be used to detect specific PCR amplified double stranded DNA product (e.g. ethidium bromide, or SYBR Green I).

ii) The 5' nuclease (TaqMan) assay can be used which utilizes a specially constructed primer whose fluorescence is quenched until it is released by the nuclease activity of the Taq DNA polymerase during extension of the PCR product.

iii) Assays based on Molecular Beacon technology can be used which rely on a specially constructed oligonucleotide that when self-hybridised quenches fluorescence (fluorescent dye and quencher molecule are adjacent). Upon hybridisation to a specific amplified PCR product, fluorescence is increased due to separation of the quencher from the fluorescent molecule.

iv) Assays based on Amplifluor (Intergen) technology can be used which utilize specially prepared primers, where again fluorescence is quenched due to self-hybridisation. In this case, fluorescence is released during PCR amplification by extension through the primer sequence, which results in the separation of fluorescent and quencher molecules.

v) Assays that rely on an increase in fluorescence resonance energy transfer can be used which utilize two specially designed adjacent primers, which have different fluorochromes on their ends. When these primers anneal to a specific PCR amplified product, the two fluorochromes are brought together. The excitation of one fluorochrome results in an increase in fluorescence of the other fluorochrome.

The above procedures can be performed using fetal cells obtained directly from maternal blood as described herein, or alternatively, following amplification of fetal cells in culture.

In the case of cultured fetal cells that may occasionally undergo somatic mutation or somaclonal variation in culture, it is preferred to conduct parallel culturing and testing of fetal cells. In accordance with such an embodiment, the detection of the same abnormality in parallel or duplicate samples of fetal cells derived from the same fetus is diagnostic of the abnormality occurring in the fetus, because the likelihood of the same somaclonal variation arising independently in two separate cultures is low.

Alternatively, or in addition, fetal cells may be derived from maternal blood taken at different stages of pregnancy or at different times during pregnancy, using the methods described herein, and tested for an abnormality. The presence of the same abnormality in more than one fetal cell sample from the same pregnant female is also indicative of the abnormality in the intact fetus, rather than a consequence of a somaclonal variation.

The present invention is further described with reference to the following non-limiting examples.

EXAMPLE 1

Enrichment of Fetal Cells from Maternal Blood

Blood samples (10 ml) from five pregnant women were obtained. Gestational ages ranged between 10 and 14 weeks, with unknown fetal gender and condition. Blood samples were processed as follows:

Nucleated cells were isolated using a density gradient. B lymphocytes and monocytes were removed using anti-CD19 and anti-CD14 magnetic beads. The remaining isolated cells were exposed for 30 min to a mixture of goat $F(ab')_2$ anti-human IgG and goat $F(ab')_2$ anti-human IgM, both of which were conjugated with the fluorescent dye phycoerythrin (PE). The cells were washed and suspended in PBS with 1% (v/v) formaldehyde, DNA-specific dye Hoechst 33342 and 0.05% (v/v) Triton X100.

The nucleated cells in the samples (5-10 million per sample) were subjected to fluorescence-activated cell sorting (FACS), to isolate Hoechst$^+$/PE$^+$ cells (i.e. cells having normal DNA content and that bind to PE-conjugated antibody fragments). The threshold level for classification of cells as being PE$^+$ was defined such that the PE$^+$ cell population comprised about 0.01% of all cells in maternal blood samples.

The flow-sorted cells (on microscope slides) were labelled by fluorescence in situ hybridisation (FISH), using probes that are specific for Y and X-chromosomes, respectively. The numbers of cells containing a Y signal (i.e., having a paternally-derived Y chromosome and being derived from a male fetus) were determined using a fluorescence microscope. Two maternal blood cell preparations produced a Y-signal. One maternal blood cell preparation contained 10 cells producing a Y-signal.

Considering that the fetal gender was not a priori known, some of the fetuses were likely to be female and their cells undetectable by Y-specific hybridization. If all sorted samples contained fetal cells, the statistical detection rate would be 50%. The detection of fetal cells producing a Y-signal in 2 out of 5 maternal blood samples tested approaches the theoretical 50% detection rate, and indicates that at least most, and maybe all, sorted samples contained fetal cells.

The concentration of fetal cells in the flow-sorted cell population was more than 1:1000. Considering that this isolation was done without prior elaboration of detailed optimum conditions, this an encouraging result and a proof of principle regarding the existence of maternal anti-fetal antibodies, as well as the utility of the method for isolating fetal cells.

EXAMPLE 2

Isolation of Reactive Maternal Antibodies from Plasma

Affinity Capture of IgG and IgM

Plasma isolated from maternal blood is first clarified (centrifuge at 10,000 g and filtered through 0.45 μm filter) and passed through a Protein-A or Protein-G column (Amersham Biosciences) to bind total human IgG. Simultaneously, the clarified maternal blood is passed through a Kaptiv-M™-Sepharose column (Interchim) or a mannin-binding protein (MBP)-Sepharose column (Nevens et al., *J. Chromatogr.* 597, 247-256, 1992; Pierce), to bind total IgM (Sisson and Castor, *J. Immunol. Methods* 127, 215-220, 1990). All steps are performed at about 4° C.

Once IgG and IgM factions are bound to the columns, the columns are washed with TBS, and the columns are uncoupled.

Initially, the IgG is eluted using 3M magnesium chloride/25% ethylene glycol/HEPES pH 8.0 as the mobile phase to maintain the individual IgG fractions as unbound components. Next the Protein-A or Protein-G column is uncoupled from the pumping system and the Kaptiv-M column is reconnected. The IgM bound column is washed with TBS and the IgM is eluted using the same buffer (i.e., 3M magnesium chloride/25% ethylene glycol/HEPES pH 8.0) as the mobile phase to maintain the individual IgM fractions as unbound components.

MBP-Sepharose columns are used at 4° C. to maintain binding of IgM. After binding, the column is removed from the cold to equilibrate at room temperature and IgM elution buffer is added and allowed to incubate on the column for 30 min. After incubation, IgM is eluted, and fractions are buffer-exchanged using PD-10 or Fast-desalting columns to the preferred buffer for further use.

Following elution, individual fractions from each column are covalently coupled to activated CNBr—Sepharose or NHS-Sepharose using standard conditions (see protocol 1 below).

Size-exclusion Chromatography Separation of Immunoglobulins

Plasma isolated from maternal blood is first clarified (centrifuge at 10,000 g and filter through 0.45 μm filter) then treated with caprylic acid to precipitate the bulk of plasma proteins without affecting Ig and some a2-macroglobulins.

The Ig fraction is then precipitated with ammonium sulfate (Tsang and Wilkins, *J. Immunol. Meth.* 138, 291-299, 1991). Following precipitation, the Ig fraction is redissolved in HEPES buffer and adjusted to a final buffer composition of 3M magnesium chloride/25% (v/v) ethylene glycol/HEPES pH 8.0.

This resuspended Ig fraction is then subjected to size-exclusion chromatography (Coppola et al., *J. Chromatogr.* 476, 269-290, 1989; Folkersen, et al., *J. Immunol. Methods* 23, 127-135, 1978) on Superose-6 (Pharmacia), using 3M magnesium chloride/25% (v/v) ethylene glycol/HEPES pH 8.0 as the mobile phase to maintain the individual Ig fractions (IgM and IgG) as unbound components.

After elution of IgM and IgG as separate fractions, the individual fractions are then coupled to activated CNBr—Sepharose or NHS-Sepharose using standard conditions (see protocol 1 below).

If the class and size of the anti-foetal cell antibodies and their anti-idiotypic antibody counterparts are different from each other, these isolated antibodies can then be desalted by batch wise column desalting on PD-10 columns or FAST-desalting columns (Amersham Biosciences) using TBS as the mobile phase in-order to provide unbound antibody for further use.

If antibodies are to be purified in a manner where binding to CNBr- or NHS-Sepharose is not required to initially covalently couple the antibody preparation in order to maintain separation of antibodies from their anti-idiotypic antibody counterparts, and maximal efficiency orientated-antibody coupled to beads are required, protocol 2 below is preferably used.

Free-flow Electrophoresis of Immunoglobulin Fraction Under Denaturing Conditions Plasma isolated from maternal blood is first clarified (centrifuge at 10,000 g and filter through 0.45 μm filter) then treated with caprylic acid to precipitate the bulk of plasma proteins without affecting Ig and some $\alpha_2$-macroglobulins. The Ig fraction is then precipitated with ammonium sulfate (Tsang and Wilkins, *J. Immunol. Meth.* 138, 291-299, 1991).

Following isolation, the Ig fraction is redissolved in 0.1M Tris/0.2% Hydroxypropylmethyl cellulose/0.2% (v/v) ampholytes/2-6M urea. This solution is then applied to free-flow electrophoresis (FFE) device (Octopus, Tecan) for separation by continuous solution-phase isoelectric focusing (Hoffmann et al., *Proteomics.* 1, 807-818, 2001). Fractions (resolution 0.01-0.05 pH units per fraction) are then buffer-exchanged into PBS, using PD-10 or fast-desalting columns (Amersham Biosciences). Alternatively, fractions are transferred into 3M magnesium chloride for coupling to CNBr-Sepharose or NHS-Sepharose for further use.

Protocol 1: Covalent Coupling of Protein to CNBr-activated Sepharose.

1. Weigh out the required amount of freeze dried powder (1 g freeze-dried powder gives about 3.5 ml final volume) and suspend in 1 mM HCl. The medium swells immediately and should be washed for 15 minutes with 1 mM HCl on a sintered glass filter (porosity 1 is recommended). Use approximately 200 ml 1 mM HCl per gram freeze-dried powder, added in several aliquots.
2. Concentrate the antibody preparation in 3M magnesium chloride/25% ethylene glycol at pH 8.0 to about 5 mg/mL using centrifugal concentrators with 100K MWCO membranes (Ultrafree-15, Millipore). Use about 5 ml antibody solution per gram freeze dried powder.
3. Mix the antibody preparation in a falcon tube. Rotate the mixture end-over-end for 1 h at room temperature or overnight at 4° C. Other gentle stirring methods may be employed. Do not use a magnetic stirrer.
4. Wash away excess ligand with at least 5 medium (gel) volumes of coupling buffer.
5. Block any remaining active groups with an amine buffer. Transfer the medium to 0.1 M Tris-HCl buffer, pH 8.0 or 1 M ethanolamine, pH 8.0. Let it stand for 2 hours.
6. Wash the medium with at least three cycles of alternating pH. Wash with at least 5 medium volumes of each buffer. Each cycle should consist of a wash with 0.1 M acetate buffer, pH 4.0 containing 0.5 M NaCl followed by a wash with 0.1 M Tris-HCl, pH 8 containing 0.5 M NaCl.
7. Store the beads at 4° C. when not in use.

Protocol 2: Directed Orientation of Antibodies on an Antibody Affinity Resin

The conventional method of immobilizing antibodies on solid matrices, employing cyanogen bromide-activated Sepharose, often generates affinity columns with low antibody activity, because the immunoglobulin molecules are oriented randomly and attached at multiple sites to the Sepharose, which reduces the efficiency of antibody/antigen interactions. This protocol describes the directed coupling of antibody to Protein G-agarose via its Fc domain, and subsequent covalent crosslinking of the complex using dimethyl pimelimidate (DMP). Protein G binds to the Fc portion of immunoglobulin molecules, which allows optimal spatial orientation of antibodies and maximum antigen binding efficiency. While this protocol is written for a 1-ml column, it can easily be adjusted for a batch mode/solution coupling.

1. Reagents

1. Crosslinking buffer: The crosslinking buffer is 0.1 M triethanolamine (pH 8.5) or other non-amine containing buffer at pH 7-9.
2. Dimethyl pimelimidate (DMP) solution: Prepare 10 ml of 20 mM DMP (Pierce) in 0.1 M triethanolamine (pH 9.5; the pH of the solution will decrease to ~8.0 due to the acidity of DMP). This reagent is prepared immediately before use.
3. Phosphate-buffered saline (PBS): 20 mM phosphate buffer, 150 mM NaCl, pH 7.4.
4. Stop solution: The stop solution is 0.1 M ethanolamine or an amine-containing solution like Tris or glycine. Add at a 1:4 ratio to the sample to stop the reaction.
5. Filter syringe (0.2 µm low-protein binding, Durapore from Millipore, or equivalent).
6. On-line UV detector (e.g., Pharmacia Monitor UV-1 or UV-M II).
7. Protein G column (1-ml HiTrap Protein G column containing protein G immobilized to 6% highly cross-linked spherical agarose, (Amersham Biosciences) or free beads for batch mode. The protein G content of the swollen gel is 2 mg/ml and the binding capacity for human IgG is >20 mg/ml drained gel. The gel is supplied pre-packed in columns with a bed volume of 1 ml or 5 ml equilibrated in 25% ethanol as a preservative (columns should be stored at 4-30° C.).
8. 100K Ultrafitration device (Millipore)

2. Method

1. Buffer exchange unliganded antibody to PBS or coupling buffer and adjust the concentration to ~1 mg/mL.
2. Equilibrate the Protein G column with 20 column volumes of PBS using a peristaltic pump at a flow rate of 0.5 ml/minute.
3. Pump antibody solution onto the column at a flow rate of 0.5 ml/minute.
4. Wash the column extensively with PBS and monitor the collected fractions for absorbance at 254 nm or 280 nm using an on-line UV detector. If >75% of the antibody binds to protein G Sepharose then proceed with the remainder of the protocol. If the antibody binds only weakly and "dribbles off" of the Protein G column, then abort this protocol. Collect the fractions and couple the antibody to a matrix in a non-orientated form using either cyanogen bromide activated Sepharose or N-hydroxysuccinimide activated Sepharose.
5. Equilibrate the antibody-coupled column with ~10 ml of crosslinking buffer (10 column volumes) using a peristaltic pump at a flow rate 0.5 ml/minute.
6. Pump about 5 ml of freshly prepared DMP solution through the column at 0.5 ml/minute and let it stand for 10 minutes.
7. Pump another 2.5 ml of DMP solution through the column and let it stand for another 10 minutes.
8. Pump the remaining DMP solution through the column and let it stand for a final 10 minutes.
9. Wash the column with 5 column volumes of crosslinking buffer.
10. Stop the reaction with 5 column volumes of stop solution (e.g., 0.1 M ethanolamine).
11. Equilibrate the column with ~20 column volumes of PBS supplemented with 0.02% sodium azide. The column is now ready for immunoaffinity capture studies
12. Store the column at 4° C. when it is not in use.

EXAMPLE 3

Dissociation of Soluble HLA Antigens from Anti HLA Antibodies

Plasma isolated from maternal blood is first treated with caprylic acid to precipitate the bulk of plasma proteins without affecting Ig and some $\alpha_2$ macroglobulins. Following this initial precipitation, the supernatant is taken off and then the Ig fraction is precipitated with ammonium sulfate (Tsang and Wilkins, *J. Immunol. Meth.* 138, 291-299, 1991).

Following isolation, the Ig fraction is redissolved in HEPES pH 7.2 and then made up to 3M magnesium chloride/25% ethylene glycol/HEPES pH 7.2. This solution is then rapidly desalted from the magnesium chloride and peptide HLA antigens by batch-wise column desalting on PD-10 columns or FAST-desalting columns (Amersham Biosciences) using Tris-buffered saline as the mobile phase (note PBS cannot be used at this stage as magnesium chloride will precipitate phosphate based buffers). The high-molecular weight fraction obtained is essentially free of peptide HLA antigens and is desalted ready for further use.

EXAMPLE 4

Detachment of Bound Antibodies and Antibody Complexes from the Fetal Cell-surface Non-covalently bound proteins are rapidly detached from isolated fetal cells to yield viable fetal cells, by using the following methods.

1. Trypsinization of Cell-surface Proteins

Cells obtained from maternal blood preparations are incubated with a 0.1% (w/v) trypsin/0.02% (v/v) Versene solution in PBS, and incubated at 37° C. for about 1-5 min or longer, depending upon the extent of cleavage required to abolish bound antibody without losing cell viability.

Once digestion is complete, the cells are washed to remove trypsin, possibly with a buffer comprising trypsin inhibitor.

2. Mixed-protease Cell Surface Digestion

Cells obtained from maternal blood preparations are incubated with a mixture of 0.1% (w/v) proteolytic enzymes (e.g., trypsin, pronase, elastase, collagenase and chymotrypsin) in PBS and incubated at 37° C. for 1-5 min or longer depending upon the extent of cleavage required to abolish bound antibody without loss of cell viability.

Once digestion is complete, the cells are washed to remove enzymes, possibly with enzyme-neutralizing agents such as, for example, a protease inhibitor cocktail comprising phenyl methyl sufonyl fluoride (PMSF), leupeptin, and trypsin inhibitor.

3. Cell-surface Disulfide Reduction

To perform dithiothreitol (DTT) or Tris(2-carboxyethyl) phosphine (TCEP) reduction, isolated cells from maternal blood are cultured under established conditions and then washed with 1×PBS. After washing, PBS comprising 1 mM-50 mM DTT or 0.1 mM-50 mM TCEP is added to the cells, which are incubated for 1-30 min. Cells are then washed three times in PBS and then placed in a culture media to maintain cell viability.

What is claimed is:

1. A method of identifying a fetal cell in a maternal blood sample, the method comprising:
   a) obtaining a sample of maternal blood that contains one or more fetal cells; and
   b) detecting and distinguishing a maternal antibody from the mother bound to a paternally inherited fetal antigen on the fetal cell which formed a fetal cell-maternal antibody complex, to thereby identify the fetal cell.

2. The method of claim 1, wherein step b) comprises contacting the maternal antibody bound to a fetal cell with an agent capable of forming a complex with the maternal antibody.

3. The method of claim 2, wherein the agent is detectably labelled.

4. The method of claim 3, wherein the label is used to detect the fetal cell-maternal antibody complex.

5. A method of identifying a fetal cell in a sample, the method comprising:
   a) contacting cells isolated from maternal blood sample with maternal antibodies, and
   b) detecting and distinguishing a maternal antibody from the mother which bound to a paternally inherited fetal antigen on a fetal cell thus forming a fetal cell-maternal antibody complex to thereby identify the fetal cell, wherein the maternal antibodies comprise maternally produced antibodies specific for paternally- inherited fetal antigens.

6. The method according to claim 5, wherein the maternal antibodies are prepared by a process comprising dissociation of antibodies from a complex with a soluble HLA antigen and/or an anti-idiotypic antibody.

7. The method of claim 5, wherein step b) comprises contacting the maternal antibody bound to a fetal cell with an agent capable of forming a complex with the maternal antibody.

8. The method according to claim 7, wherein the agent is an antibody or antibody fragment.

9. The method according to claim 7, wherein the agent is a polypeptide that binds to an immunoglobulin.

10. The method of claim 9, wherein the polypeptide is selected from the group consisting of, protein A, protein G, and protein L.

11. The method according to claim 7, wherein the agent is detectably labelled.

12. The method of claim 11, wherein the label on the agent is used to detect the fetal cell maternal antibody complex.

13. The method according to claim 12, wherein the label is selected from the group consisting of:
   a fluorescent label, a radioactive label, a paramagnetic particle, a chemoluminescent label, and an enzymatic label.

14. The method of claim 13, wherein the label is a paramagnetic particle and wherein the step of detecting the fetal cell-maternal antibody complex comprises contacting the detectable agent labeled fetal cell-maternal antibody complexes to a magnet.

15. The method according claim 13, wherein the label is a fluorescent label and wherein the step of detecting the fetal cell-maternal antibody complex comprises performing fluorescence activated cell sorting.

* * * * *